United States Patent
Mikus et al.

[11] Patent Number: 6,162,231
[45] Date of Patent: Dec. 19, 2000

[54] STENT INSERTION DEVICE

[75] Inventors: Paul W. Mikus; Jay J. Eum, both of Aliso Viejo, Calif.

[73] Assignee: Endocare, Inc., Irvine, Calif.

[21] Appl. No.: 09/336,974

[22] Filed: Jun. 21, 1999

Related U.S. Application Data

[63] Continuation-in-part of application No. 09/152,557, Sep. 14, 1998, Pat. No. 6,093,194.

[51] Int. Cl.⁷ ........................................ A61F 11/00
[52] U.S. Cl. .............................. 606/108; 606/99; 604/164
[58] Field of Search .................... 606/108, 198, 606/99; 604/164; 623/1.12, 1.11

[56] References Cited

U.S. PATENT DOCUMENTS

| | | | |
|---|---|---|---|
| 3,868,956 | 3/1975 | Alfidi et al. | 128/345 |
| 4,503,569 | 3/1985 | Dotter | 3/1.4 |
| 4,994,066 | 2/1991 | Voss | 606/108 |
| 5,026,377 | 6/1991 | Burton et al. | 606/108 |
| 5,224,953 | 7/1993 | Morgentaler | 606/192 |
| 5,433,723 | 7/1995 | Lindenberg et al. | 606/198 |
| 5,562,641 | 10/1996 | Flomenblit et al. | 604/281 |
| 5,591,172 | 1/1997 | Bachmann et al. | 606/108 |
| 5,601,591 | 2/1997 | Edwards et al. | 606/198 |
| 5,607,466 | 3/1997 | Imbert et al. | 623/1 |
| 5,667,522 | 9/1997 | Flomenblit et al. | 606/198 |
| 5,766,237 | 6/1998 | Cragg | 623/1 |
| 5,782,838 | 7/1998 | Beyar et al. | 606/108 |

*Primary Examiner*—Michael Buiz
*Assistant Examiner*—Anthony King
*Attorney, Agent, or Firm*—Lyon & Lyon LLP

[57] ABSTRACT

Two embodiments for a stent delivery device are disclosed. In the first embodiment, the stent delivery device comprises an outer sheath and an inner tubular member which distally ends in a tongue having an arcuate cross section. In a second embodiment, the stent delivery device further comprises a housing having a lumen extending longitudinally therethrough, the lumen holding the inner tubular member. A guide pin attached to the outer sheath is slidably disposed within the housing wherein the guide pin may be longitudinally displaced with respect to the lumen. In addition, an endoscope mounting plate may be slidably disposed along the housing. Detents may be used to releasably prevent a proximal displacement of the guide pin within the lumen of the housing as well as to releasably prevent the proximal displacement of the endoscope mounting plate with respect to the housing.

7 Claims, 9 Drawing Sheets

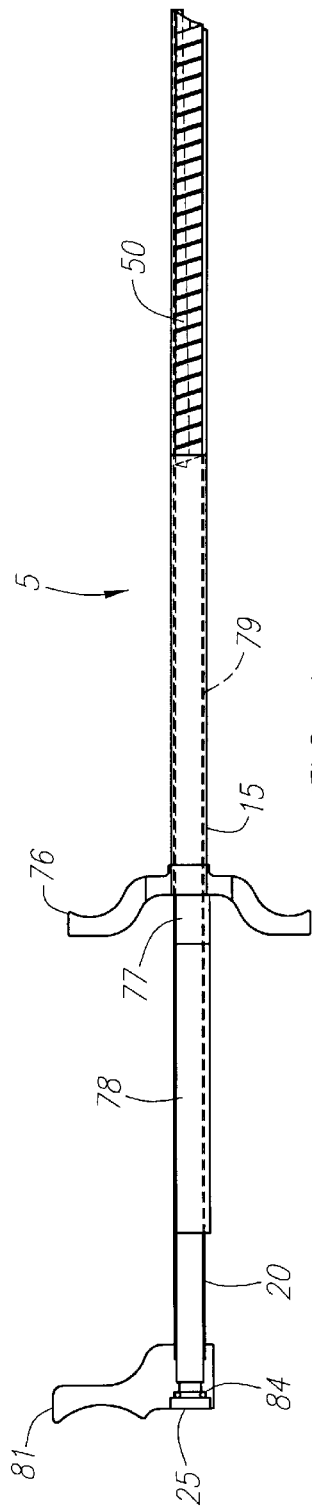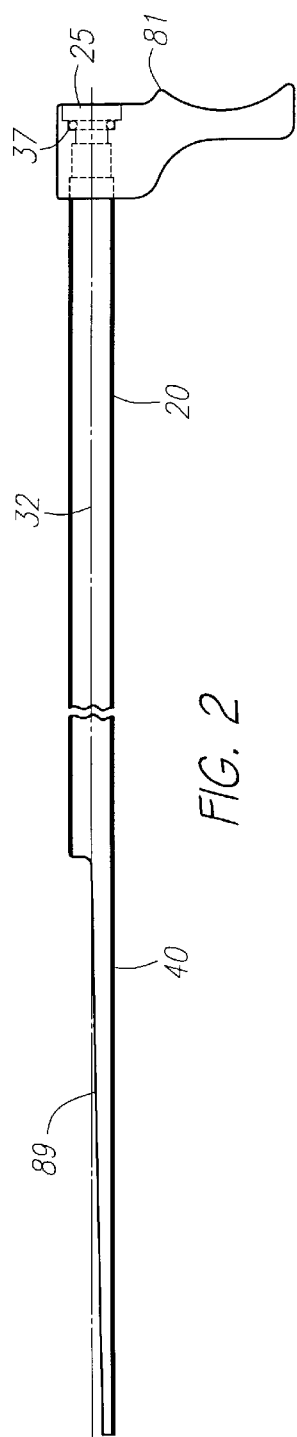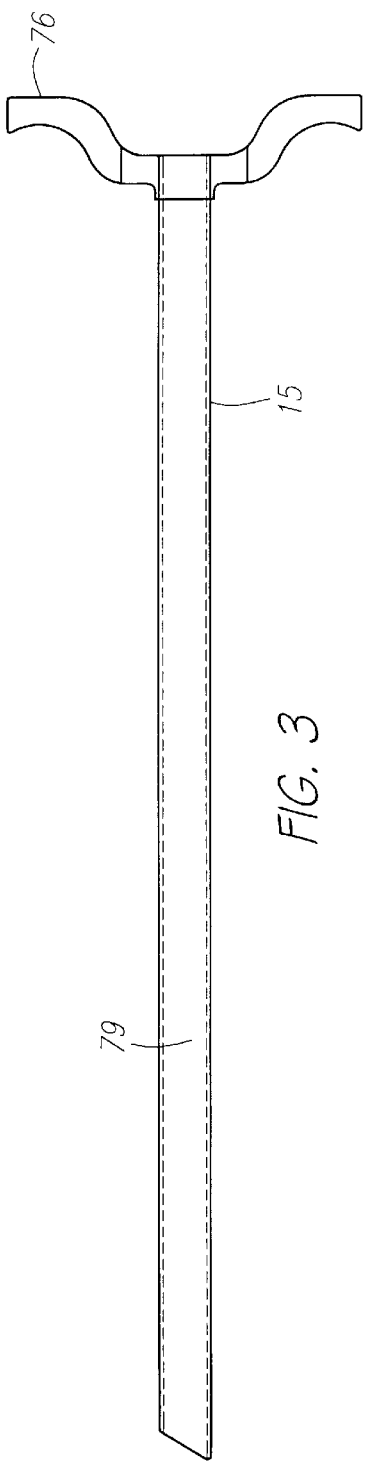

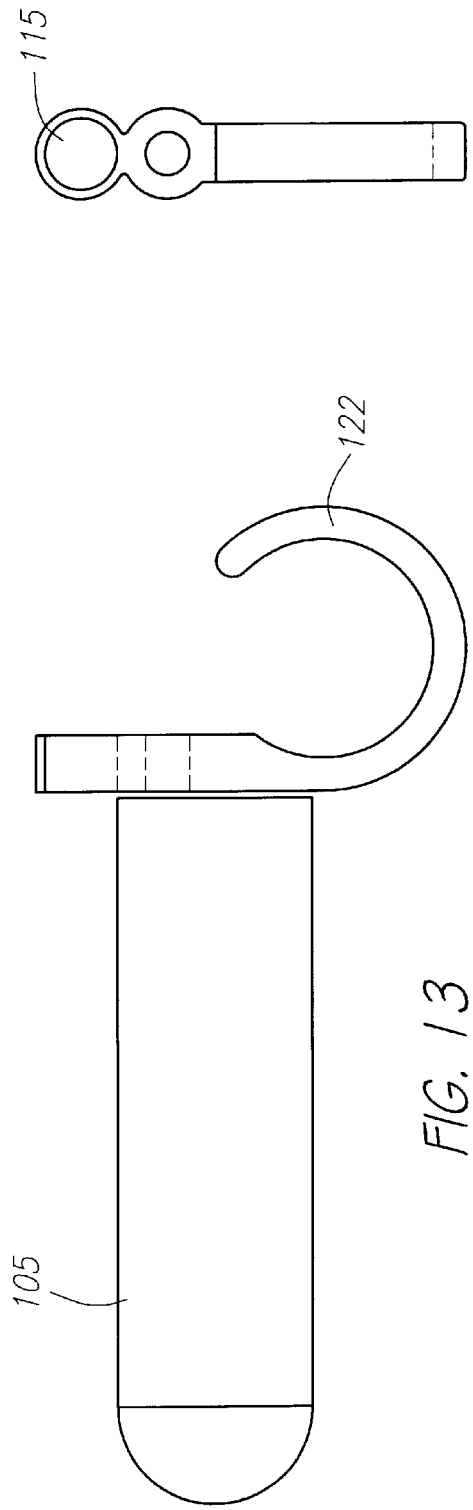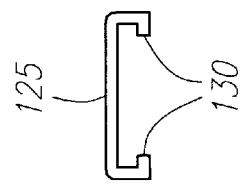

STENT INSERTION DEVICE

RELATED U.S. APPLICATION DATA

This application is a continuation-in-part of U.S. application Ser. No. 09/152,557, filed Sep. 14, 1998, now U.S. Pat. No. 6,093,194, the contents of which are hereby incorporated by reference.

INTRODUCTION

This invention relates to stent delivery systems to facilitate the treatment of prostate disease, including benign prostate hypertrophy or prostate cancer.

BACKGROUND OF THE INVENTION

Benign prostate hypertrophy, also known as benign prostate hyperplasia (BPH), commonly afflicts men beginning at age 50. The prostate swells and presses on the urethra, making urination difficult and uncomfortable. In addition, it may cause urination urgency. Also afflicting older men is prostate cancer which may metastasize and cause death. Early treatment can reduce the risks of death from prostate cancer.

Both prostate enlargement and prostate cancer may be treated with heat treatments such as hyperthermia or thermotherapy. A stent may serve the dual purpose of acting as a heat source for the thermotherapy procedures, as well as acting to hold the urethra open after therapy to temporarily prevent blockage due to swelling and prostate tissue sloughing. Additionally, a stent may be implanted temporarily while the patient awaits more aggressive surgery or treatment. Rather than implantation after thermotherapy, a stent may be implanted temporarily after cryosurgery or hypothermia. Finally, a stent may be implanted as a primary treatment.

Given the number of therapies employing urethral stents, there is a need in the art for improved stent delivery systems. Eum, U.S. application Ser. No. 09/063,118, filed April 20, 1998, and incorporated herein by reference, discloses a stent delivery system comprising a catheter with an anchoring mechanism at its distal end that is placed within the bladder. The stent is displaced proximally on the catheter a predetermined distance from the anchor. This ensures that the stent does not affect the bladder sphincter. Placement of a stent within the bladder sphincter could lead to incontinence and other problems. Because the anchoring mechanism must be placed within the bladder, such a stent delivery system requires a flexible endoscope. Many doctors, however, are equipped only with standard rigid urological endoscopes, which cannot maneuver through the prostatic urethra into the bladder. Thus, there is a need in the art for improved stent delivery systems that can accurately and conveniently implant a stent in the prostatic urethra using conventional rigid urological endoscopes.

SUMMARY OF THE INVENTION

The stent delivery systems described below permit placement of a stent in the urethra. The devices efficiently implant a stent into the prostatic urethra under direct vision. The invention has two main embodiments.

In a first embodiment, the invention comprises a single-petaled catheter including an outer sheath having a first predetermined length and an inner tubular member having a second predetermined length wherein the second predetermined length is greater than the first predetermined length. The inner tubular member is formed to be slidably disposed within the outer sheath and ends distally in an elongated tongue having an arcuate cross section. The clinician guides the distal end of the catheter into position using an endoscope inserted within the lumen of the inner tubular member and/or using ultrasonic or x-ray imaging. After positioning the catheter, the clinician proximally displaces the outer sheath to expose the tongue of the inner tubular member. The distal end of the stent expands against the now exposed tongue to begin gripping the urethral wall. When satisfied with the final stent position, the clinician proximally withdraws the inner tubular member away from the stent, using the distal end of the outer sheath to prevent proximal displacement of the stent. The outer sheath may then be withdrawn, completing the stent deployment.

The invention further comprises a stent delivery device for delivering a stent using a single-petaled catheter comprising an inner tubular member partially disposed within an outer sheath. The stent delivery device comprises a housing having a lumen extending longitudinally therethrough, the lumen ending proximally in a port for receiving an endoscope, the lumen adapted for receiving the inner tubular member. A pin is slidably engaged within the housing wherein the pin may be longitudinally displaced with respect to the central axis of the lumen. The pin is attached to the proximal end of the outer sheath such that the outer sheath may be slidably disposed over the tubular member. The housing includes at least one detent coupled to the pin such that distal displacement of the pin with respect to the housing is releasably prevented.

In another innovative aspect, the present invention includes a method of placing a stent within a prostatic urethra, the method including the step of providing the previously-described stent delivery device. The method further comprises the steps of inserting the outer sheath through the urethra into the prostatic urethra; proximally displacing the guide pin of the stent delivery device a first distance with respect to the central axis of the lumen whereby the outer sheath is displaced the first distance with respect to the tubular member wherein a distal portion of the stent is deployed in the prostatic urethra but does not resist further displacement. A clinician may then verify the proper location of the stent within the prostatic urethra before proceding with the remaining steps in the method. The clinician may then proximally displacing the guide pin a second distance with respect to the central axis of the lumen whereby the outer sheath is displaced the second distance with respect to the tubular member to fully expose the tongue of the tubular member whereby the stent contacts the prostatic urethra substantially along the full length of the stent. To fully deploy the stent within the urethra, the clinician may then proximally displacing the housing while steadying the guide pin of the stent delivery device wherein the tubular member is proximally displaced with respect to the outer sheath whereby the tongue of the tubular member is retracted from the stent.

DESCRIPTION OF THE DRAWINGS

FIG. 1 is a side elevational view, partially cut-away, of a single-petaled embodiment of a stent deployment device in accordance with the present invention.

FIG. 2 is a side elevational view of the inner tubular member of the stent deployment device shown in FIG. 1.

FIG. 3 is a side elevational view of the outer sheath of the stent deployment device shown in FIG. 1.

FIG. 13 is a side elevational view of the guide pin for the stent delivery system of FIG. 9.

FIG. 14 is a rear elevational view of the guide pin for the stent delivery system of FIG. 9, looking into the distal end.

FIG. 15 is a side elevational view of the scope mounting plate for the stent delivery system, of FIG. 9.

FIG. 16 is a rear elevational view of the scope mounting plate, looking into the proximal end.

DETAILED DESCRIPTION OF THE INVENTION

Figure 4:
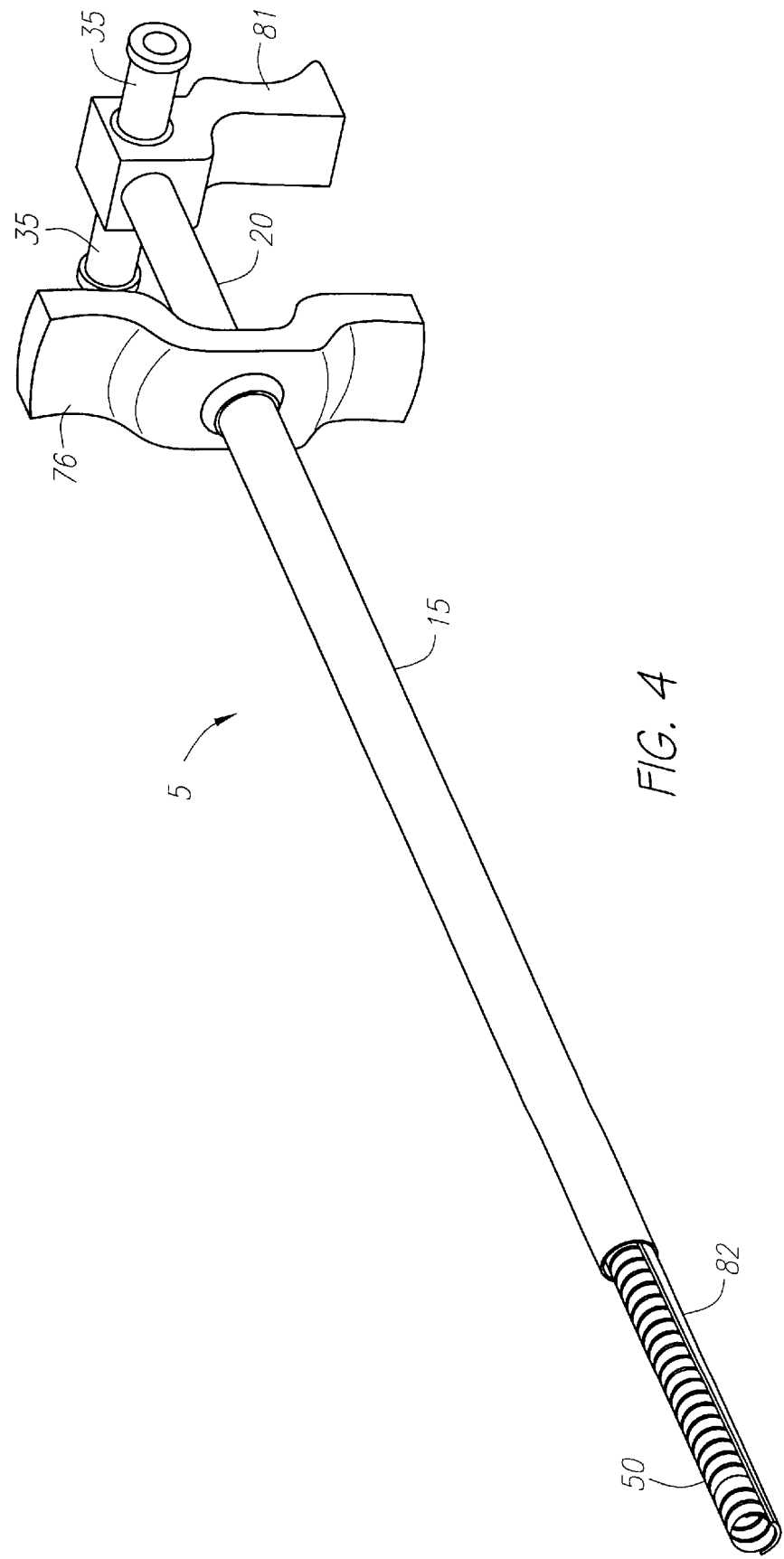
FIG. 4 is side elevational view of the stent deployment device shown in FIG. 1 with the outer sheath proximally displaced to expose the elongated tongue of the inner tubular member and the stent.

The stent deployment device according to the present invention has two main embodiments. In the first embodiment, the stent deployment device comprises a single-petaled catheter. In the second embodiment, the stent deployment device further comprises a stent delivery device that manipulates an embodiment of the single-petaled catheter. The single-petaled catheter will be described first.

The Single-petaled Catheter Embodiment

Turning now to FIGS. 1–4, the single-petaled catheter is illustrated. FIG. 1 illustrates a cross sectional view of a single-petaled catheter 5 including an outer sheath 15 and an inner tubular member 20 slidably disposed within the lumen of the outer sheath 15. Inner tubular member 20 has an adapter port 25 for the introduction of a conventional endoscope 30 (illustrated in FIGS. 5 through 8) into the lumen 32 of inner tubular member 20. Saline or other suitable fluids may be pumped into the lumen 32 of inner tubular member 20 through luer ports 35. Seal 37 prevents leakage of fluid from adapter port 25.

The distal end of inner tubular member 20 is formed into an elongated tongue 40 having an arcuate cross section. Thus, because the tongue 40 resembles a single flower petal, this embodiment is denoted as a single-petaled catheter 5. Inner tubular member 20 and tongue 40 may be constructed out of a rigid material, preferably medical grade polycarbonate or similar plastic. Because tongue 40 and inner tubular member 20 are rigid, outer sheath 15 may be constructed of polycarbonate plastic also yet still possess suitable rigidity to protect often-fragile endoscopes during insertion of catheter 5 into the urethra. Manufacturing outer sheath 15 from polycarbonate plastic rather than steel not only is cheaper but also offers less friction to movements of stent 50. Although a steel outer sheath may be used, such an outer sheath would grip stent 50 more firmly, thus hampering stent deployment, because of the greater friction which would exist between the steel outer sheath and stent 50.

Elongated tongue 40 preferably has an arcuate cross section, more preferably approaching 180° in arc. Thus, in this preferred embodiment, tongue 40 is a longitudinally divided half of tubular member 20. However, the width and arc of tongue 40 may range widely without departing from the spirit of this invention. Indeed, tongue 40 could approach a flattened columnar shape. Those of ordinary skill in the art will appreciate the range of shapes tongue 40 could have while still maintaining its function. The longitudinal length of tongue 40 should extend substantially along the length of stent 50, more preferably along the fall length of stent 50 as illustrated in FIGS. 1 and 4.

Prior to deployment, helical-shaped stent 50 lies coiled between the inner surface 89 of tongue 40 and the inner lumen wall 79 of outer sheath 15 as illustrated in FIGS. 1 and 4. Thus, tongue 40 receives and supports stent 50 within the lumen of outer sheath 15 but does not envelop stent 50. In addition, the lumen of inner tubular member 20 is sized such that stent 50 cannot displace proximally past tongue 40 into the lumen of inner tubular member 20. Tongue 40 greatly reduces the friction between stent 50 and the outer sheath 15, thereby assisting the stent deployment process.

Before deployment, stent 50 is in the martensitic or compressed stage. In FIG. 4, outer sheath 15 is displaced proximally with respect to stent 50 and tongue 40. In the urethra, this would expose the stent 50 to body heat, causing the stent 50 to transition to an austenitic or expanded state. Alternatively, warm saline pumped down luer ports 35 could assure that stent 50 transitions into the austenitic stage. The stent 50 in the single-petaled catheter 5 has substantial contact with the inner lumen wall 79 of outer sheath 15. This is not a problem, however, because the polycarbonate material of outer sheath 15 offers little resistance to movements of stent 50.

Restrainers 77 and 78 are placed on single-petaled catheter 5 to prevent premature displacements of outer sheath 15 during insertion of the catheter 5 into the penis 51 and prostatic urethra 53. As illustrated in FIG. 1, tubular member 20 has a greater length than outer sheath 15. Thus, when tubular member 20 is inserted into outer sheath 15 so that the distal end of tongue 40 is substantially aligned with the distal end of outer sheath 15, tubular member 20 will have a proximal extension extending proximally from handle 76 of outer sheath 15. Outer sheath 15 could be displaced proximally on this proximal extension of tubular member 20. Handle 81 on the tubular member 20 acts as a stop when contacting handle 76, preventing further distal displacement of the inner tubular member 20 within the outer sheath 15. Similarly, restrainers, which clamp about the surface of this proximal extension of tubular member 20 prevent any premature proximal displacement during insertion of catheter 5 into the urethra. In one embodiment, restrainers 78 and 77 clamp about the proximal extension of tubular member 20. Restrainers 78 have an appropriately shaped arcuate cross section to facilitate clamping about tubular member 20. Those of ordinary skill will appreciate the widely varying shapes restrainers 78 and 77 could have while still retaining their clamping function.

Figure 5:
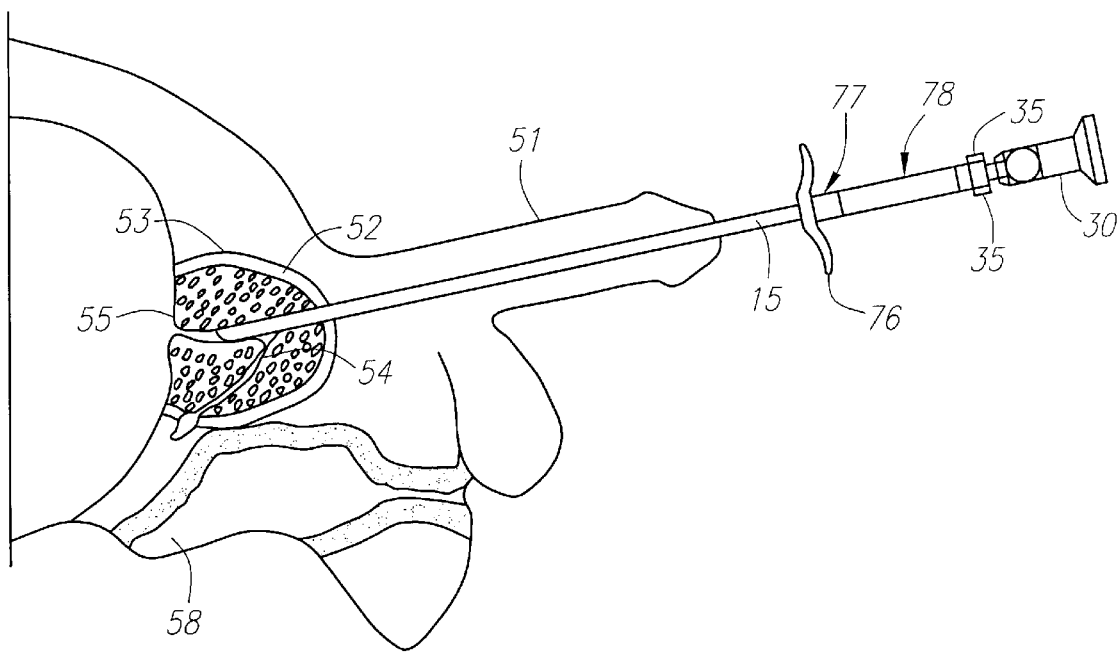
FIG. 5 is a cross sectional view of the stent deployment device of FIG. 1 in position to begin stent deployment.

FIGS. 5 through 8 illustrate a stent deployment method using the single-petaled catheter embodiment. FIG. 5 illustrates the insertion of the catheter 5 through the penis 51 into the prostatic urethra 53. Using endoscope 30, the clinician determines that the distal end of the outer sheath 15 is proximal to the bladder sphincter 55 and distal to the seminal vesicles 54. Saline or other suitable fluid pumped down the lumen of tubular member 20 through luer ports 32 assists the endoscopic imaging of the distal end of outer sheath 15. In addition, the clinician may verify the location of catheter 5 with respect to the prostatic urethra 53 by using ultrasonic imaging. Such imaging would require, for example, an ultrasound transducer to be placed in the rectum 58. Instead of ultrasonic imaging or in addition thereto, the clinician could employ x-ray imaging to verify the location of catheter 5 within prostatic urethra 53. Satisfied that the catheter has been properly placed within prostatic urethra 53, the clinician may begin initial deployment of stent 50.

Figure 6:
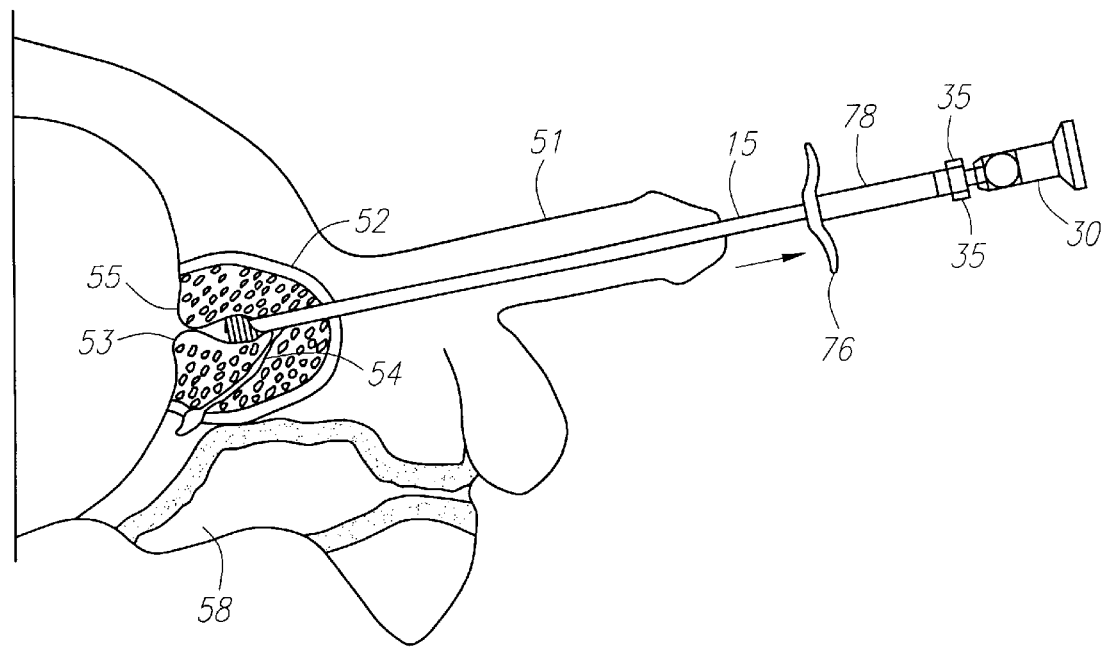
FIG. 6 is a cross sectional view of the stent deployment device of FIG. 1 in the initial deployment stage.

Initial deployment of stent 50 by single-petaled catheter 5 is illustrated in FIG. 6. Restrainers 77 that had been placed about the proximal extension of tubular member 20 are removed. The clinician then displaces outer sheath 15 proximally as shown in FIG. 6. Restrainers 77 are sized so that the proximal displacement of outer sheath 15 exposes only a few coils at the distal end of helically shaped stent 50. Having reached its austenitic state either by sensing body temperature or through exposure to warm saline pumped into luer ports 35, these coils of stent 50 expand and begin gripping prostatic urethra 53. But because only a few coils are so deployed, the clinician may check their position and coil spacing using endoscope 30 fluid and adjust if necessary before starting secondary deployment.

Figure 7:
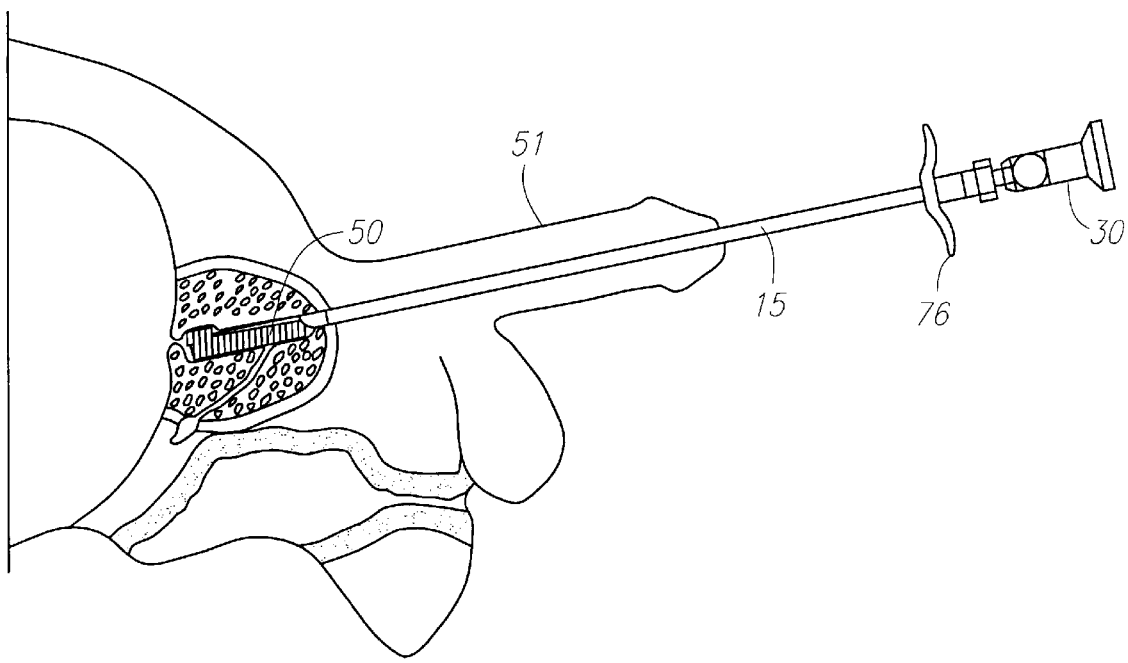
FIG. 7 is a cross sectional view of the stent deployment device of FIG. 1 in the secondary deployment stage.

Secondary deployment of stent 50 using single-petaled catheter 5 is illustrated in FIG. 7. Satisfied that the distal end of stent 50 is in proper position proximal to bladder sphincter 55 in prostatic urethra 53, the clinician removes restrainers 78. This allows a further proximal displacement of outer sheath 15 with respect to tubular member 20 whereby tongue 40 is exposed. In turn, stent 50, having reached its austenitic state, expands along the length of tongue 40 to grip the prostatic urethra 53. This allows the clinician to proceed to full deployment.

Figure 8:
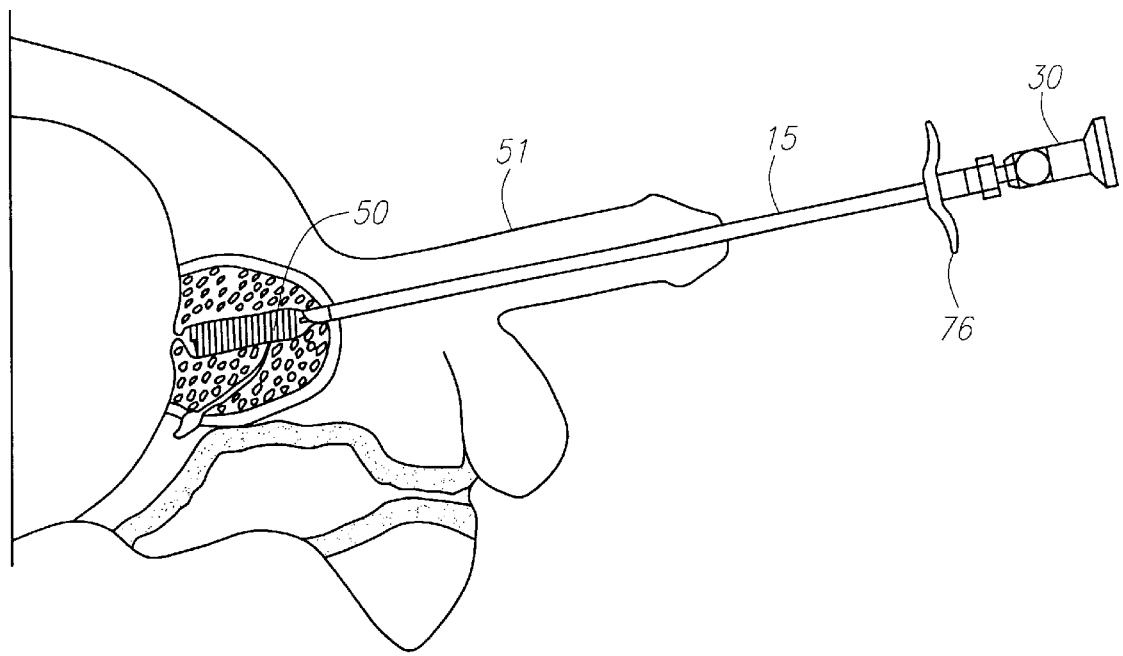
FIG. 8 is a cross sectional view of the stent deployment device of FIG. 1 in the full deployment stage.
Figure 9:
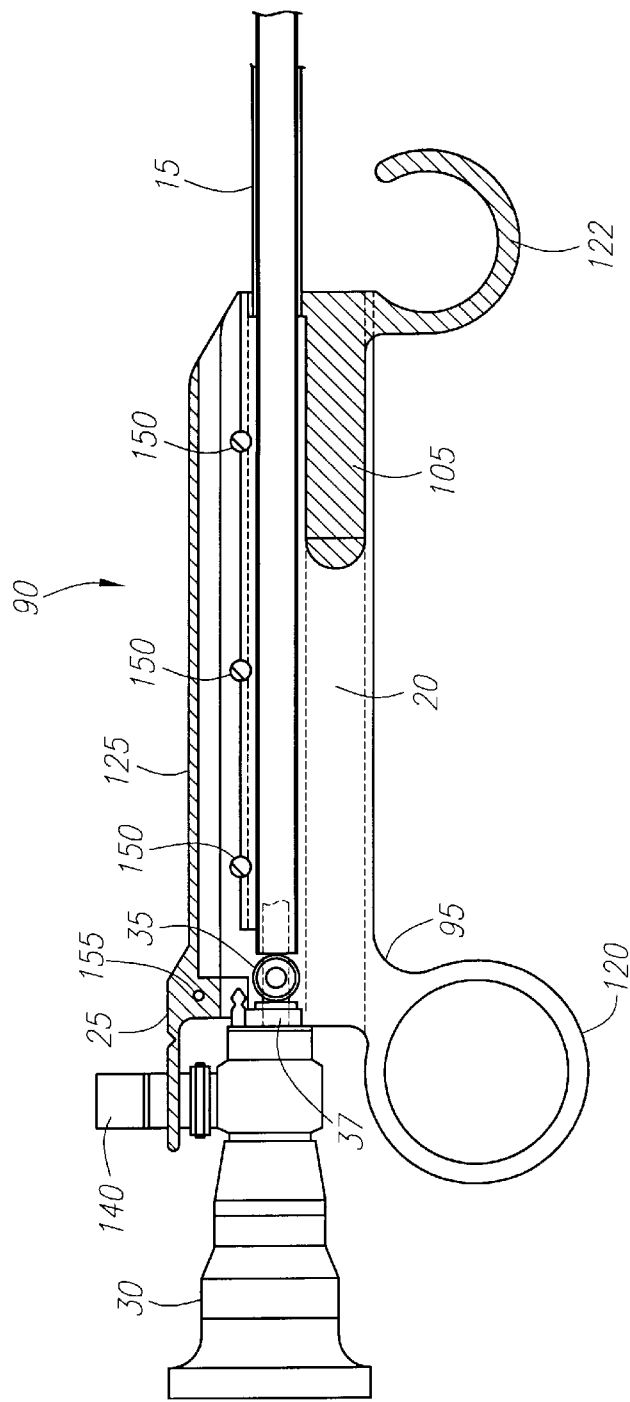
FIG. 9 is a side elevational view of a stent delivery system according to one embodiment of the invention.
Figure 10:
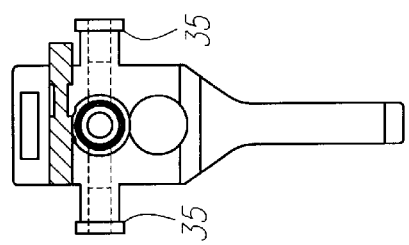
FIG. 10 is a rear elevational view of the stent delivery system of FIG. 9, looking into the proximal end.

Full deployment is illustrated in FIG. 8. The proximal end of stent 50 abuts against the to distal end of outer sheath 15. Thus, tubular member 20 may be proximally retracted with respect to outer sheath 15 without displacing stent 50 because the distal end of outer sheath 15 prevents any proximal displacement of stent 50. This stands in contrast to abi-petaled catheter 5 wherein the clinician must distally displace stent 50 during deployment. The only displacement of stent 50 during deployment using single-petaled catheter 5 occurs during the initial deployment stage illustrated in FIG. 6 wherein only a few coils at the distal end of stent 50 contact and grip the prostatic urethra 53. After the clinician is satisfied with the location of stent 50 during initial deployment, stent 50 is neither proximally nor distally displaced during the remainder of stent deployment, assuring the clinician of proper stent location. Clinicians must be careful in locating the stent in the prostatic urethra 53 because if stent 50 occludes bladder sphincter 55, the patient could be incontinent.

After proximally retracting tubular member 20 from stent 50 as illustrated in FIG. 8, stent 50 is completely deployed in prostatic urethra 53. The clinician may now withdraw single-petaled catheter 5 from penis 51 to complete stent deployment.

The Stent Delivery Device

Figure 12:
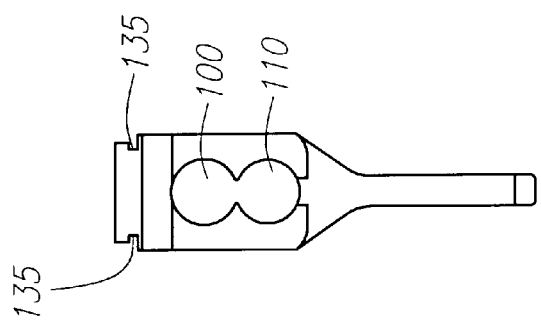
FIG. 12 is a rear elevational view of the housing for the stent delivery system of FIG. 9, looking into the distal end.
Figure 11:
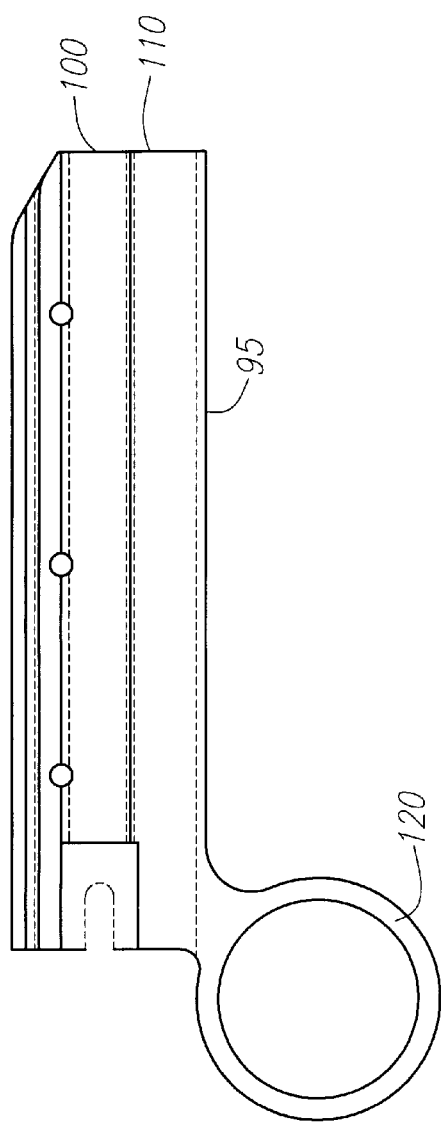
FIG. 11 is a side elevational view of the housing for the stent delivery system of FIG. 9.

In another innovative aspect, the present invention includes a stent delivery device 90 which uses a modified single-petaled catheter 5 to implant a stent within the prostatic urethra. Turning now to FIGS. 9 through 20, the stent delivery device includes a housing 95 having a lumen 100 adapted to accommodate the single petaled catheter 5. A guide pin 105 is slidably disposed within housing 95 such that the guide pin may be longitudinally displaced with respect to the lumen 100. Thus, guide pin 105 may be disposed within a secondary slot or lumen 110 which is parallel to lumen 100. As illustrated in FIG. 12, the secondary lumen 110 may communicate with lumen 100 such that a figure-8 shaped cavity is created within housing 95.

The tubular member 20 of single-petaled catheter 5 is fixed within lumen 100. Because the outer sheath 15 is held by the guide pin 105 within, for example, recess 115, the outer sheath 15 is longitudinally displaced with respect to the lumen 100 of the housing 95 if the guide pin 105 is longitudinally displaced within the secondary lumen 110. In this fashion, a clinician may displace the outer sheath 15 along the proximal extension of the tubular member 20 by displacing the guide pin 105. Because the tubular member 20 and the outer sheath 15 are held by the stent delivery device 90, the handles 76 and 81 illustrated, for example, in FIG. 1 may be eliminated. Moreover, as will be explained herein, restrainers 77 and 78, also illustrated in FIG. 1, may be eliminated because their function will be provided for by stent delivery device 90.

To assist the handling of stent delivery device 90, the housing 95 and the guide pin 105 may incorporate finger loops 120 and 122. During the initial and secondary deployment stages illustrated in FIGS. 6 and 7, the outer sheath 15 is proximally displaced along the proximal extension of the tubular member 20 without displacing tubular member 20. Because a clinician may insert his thumb within finger loop 120 of the housing 95, the clinician's index finger may pull the finger loop 122 of the guide pin 105 analogously to pulling the trigger of a gun. During such motion, it is natural for the clinician to keep his or her thumb still, thus preventing motion of the tubular member 20 during the proximal displacement of the outer sheath 15. Thus, stent deliver device 90 greatly eases the performance of the initial and secondary deployment stages of FIGS. 6 and 7.

Because the tubular member 20 is held within the housing 95, the luer ports 35 as illustrated in FIG. 4 are now located on the housing 95. Saline pumped into the luer ports 35 flows into the lumen 32 of the tubular member 20 through appropriate ports within the tubular member 20 (not illustrated). Tubular member 20 accommodates an endoscope 30 through an adapter port 25. A seal 37 prevents leakage of fluid from adapter port 25 onto the endoscope 30 as illustrated in FIG. 1. However, stent delivery device 90 provides additional support for the endoscope 30 through scope mounting plate 125. Scope mounting plate 125 has rails or flanges 130 that engage matching grooves 135 (see FIG. 12) wherein the scope mounting plate is slidably mounted on the housing 95. The endoscope 30 may be attached to the scope mounting plate, by, for example, securing post 140 of the endoscope 30 to aperture 145. The clinician may thus longitudinally displace the endoscope 30 with respect to the tubular member 20 by longitudinally displacing the scope mounting plate 125 along the grooves 135 of the housing 95.

To guard against premature displacement of the guide pin 105 within housing 95, the housing 95 may have a detent which releasably secures the guide pin 105 (and hence the outer sheath 15 which is attached to the guide pin 105) at predetermined locations within the secondary lumen 110. In one embodiment, the detent comprises a plurality of posts 150 which project partially across lumen 100. The posts 150 prevent the outer sheath 15 from being proximally displaced along the tubular member 20 held within lumen 100. Because the guide pin 105 is attached to the outer sheath 15, the guide pin 105 will be prevented from proximal displacements within lumen 110. When a clinician is ready to displace guide pin 105 by pulling the finger loop 122, the posts 150 are removed as necessary. Those of ordinary skill in the art will appreciate that many other forms of a detent could be implemented.

The scope mounting plate 125 may also be releasably secured to the housing 95 by a detent to prevent displacement of the scope mounting plate 125 along the grooves 135 of the housing 95. In one embodiment, the detent would comprise a post 155 which releasably secures the scope mounting plate 125 to the housing 95.

Figure 17:
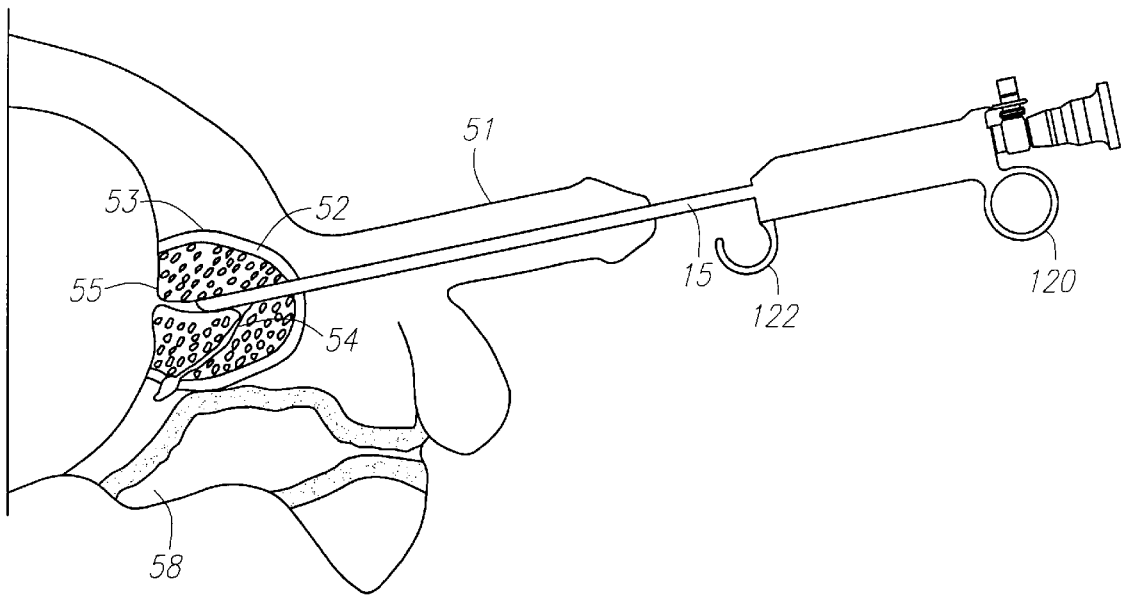
FIG. 17 is a cross sectional view of the stent deployment device of FIG. 9 in position to begin stent deployment.
Figure 18:
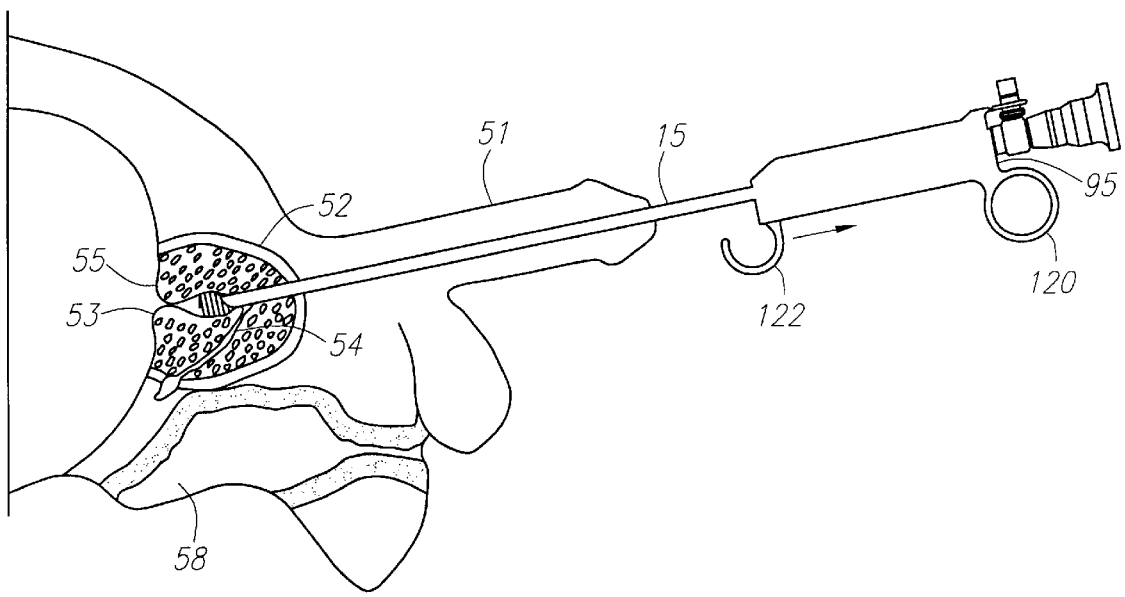
FIG. 18 is a cross sectional view of the stent deployment device of FIG. 9 in the initial deployment stage.
Figure 19:
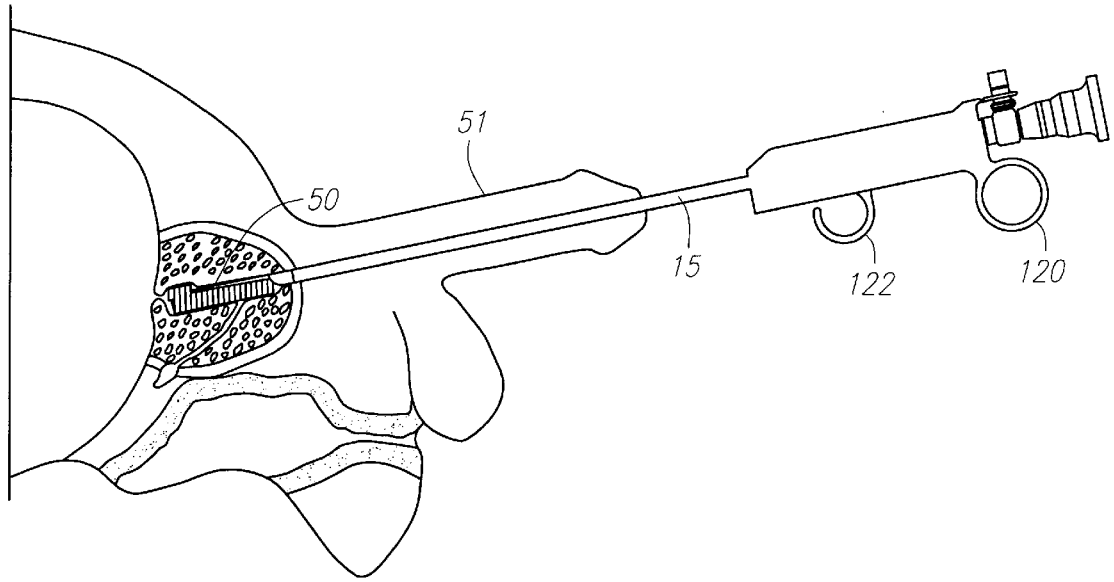
FIG. 19 is a cross sectional view of the stent deployment device of FIG. 9 in the secondary deployment stage.
Figure 20:
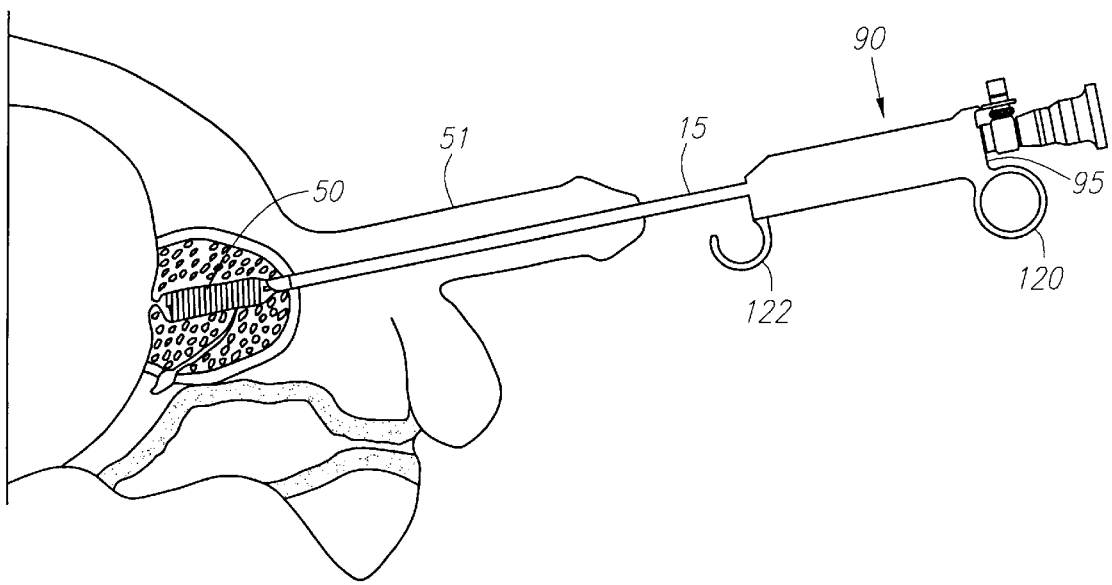
FIG. 20 is a cross sectional view of the stent deployment device of FIG. 9 in the full deployment stage.

As noted previously, the use of the stent delivery device 90 with the single-petaled catheter 5 obviates the need for the handles 76 and 81 and the restrainers 77 and 78. The initial and secondary deployment stages of stent insertion using the single-petaled catheter 5 are illustrated in FIGS. 17, 18 and 19. These steps would be performed by a clinician using the stent delivery device 90 by proximally pulling on finger loop 122, removing the posts 150 as necessary. When the clinician is ready to perform the full deployment stage of stent delivery as illustrated in FIG. 20, the clinician proximally displaces the housing 95 with respect to the guide pin 105 by proximally displacing finger loop 120 while preventing finger loop 122 from moving In this fashion the tubular member 20 is withdrawn from the stent 50 as discussed above with respect to FIG. 8. The clinician may then remove the single-petaled catheter 5 from the patient by proximally displacing the stent delivery device 90.

While various embodiments of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents.

We claim:

1. A stent delivery device comprising:
    an outer sheath extending a first predetermined distance from a distal end to a proximal end and having a first lumen therethrough;
    a tubular member extending a second predetermined distance from a distal to a proximal end with a second lumen therethrough, wherein the second predetermined distance is greater than the first predetermined distance, the tubular member being slidably disposed in the first lumen of the outer sheath and having an adapter port for receiving an endoscope at its proximal end and ending distally in an elongated tongue having an arc-shaped cross section, the elongated tongue being adapted to receive substantially the full length of a stent;
    a housing having a primary lumen extending longitudinally therethrough for receiving the proximal end of the tubular member, the primary lumen ending proximally in a port for receiving an endoscope, the primary lumen having a central axis; and
    a guide pin slidably disposed within the housing wherein the guide pin may be longitudinally displaced within the housing in parallel to the central axis of the primary lumen, the guide pin being attached to the outer sheath.

2. The stent delivery device of claim 1 further comprising an endoscope mounting plate slidably disposed along said housing.

3. The stent delivery device of claim 2 wherein said housing includes a first detent, said first detent releasably preventing longitudinal displacements of said guide pin in parallel to the central axis of the primary lumen.

4. The stent delivery of claim 3 wherein said housing includes a second detent, said second detent releasably preventing longitudinal displacements of said endoscope mounting plate with respect to the central axis of the primary lumen.

5. The stent delivery device of claim 1 further comprising:
    a stent having a distal and proximal end, said stent being disposed along said elongated tongue within the first lumen of said outer sheath, wherein the distal end of said stent, the distal end of said elongated tongue, and the distal end of said outer sheath are substantially aligned.

6. A method of placing a stent within a prostatic urethra, comprising the steps of:
    providing a stent delivery catheter comprising:
        an outer sheath extending a first predetermined distance from a distal end to a proximal end and having a first lumen therethrough;
        a tubular member extending a second predetermined distance from a distal to a proximal end and having a second lumen therethrough, wherein the second predetermined distance is greater than the first predetermined distance, the tubular member being slidably disposed in the first lumen of the outer sheath and having an adapter port for receiving an endoscope at its proximal end and ending distally in an elongated tongue having an arc-shaped cross section, said elongated tongue being adapted to receive substantially the full length of a stent;
        a housing having a primary lumen extending longitudinally therethrough for receiving the proximal end of the tubular member, the primary lumen ending proximally in a port for receiving an endoscope, the primary lumen having a central axis;
        a guide pin slidably disposed within the housing wherein the guide pin may be longitudinally displaced within the housing in parallel to the central axis of the primary lumen, the guide pin being attached to the outer sheath; and
        a stent having a distal end, the stent disposed along the elongated tongue within the first lumen of the outer sheath, wherein the distal end of the stent, the distal end of the elongated tongue, and the distal end of the outer sheath are substantially aligned;
    inserting the outer sheath through the urethra into the prostatic urethra;
    proximally displacing the guide pin a first distance within the housing whereby the outer sheath is displaced the first distance with respect to the tubular member such that a distal portion of the stent is deployed in the prostatic urethra but does resist further displacement;
    proximally displacing the guide pin a second distance within the housing whereby the outer sheath is displaced the second distance with respect to the tubular member to fully expose the tongue such that the stent contacts the prostatic urethra substantially along the full length of the stent; and
    proximally displacing the housing while steadying the guide pin whereby the tongue and tubular member are retracted from the stent such that the stent is fully deployed in the urethra.

7. The method of claim 6 wherein said stent delivery device includes an endoscope inserted in the first lumen of said tubular member, said method further comprising:

observing the position of said stent using said endoscope during said inserting step and during said proximal displacement steps.

* * * * *